United States Patent
Dixit et al.

(10) Patent No.: US 8,668,932 B2
(45) Date of Patent: Mar. 11, 2014

(54) EXTENDED RELEASE VENLAFAXINE FORMULATION

(75) Inventors: Manesh Dixit, Sunrise, FL (US); Xiu-Xiu Cheng, Weston, FL (US); Avinash Nangia, Weston, FL (US); Chin Ming Chen, Taipei (TW)

(73) Assignee: Andrx Pharmaceuticals, LLC, Davie, FL (US)

( * ) Notice: Subject to any disclaimer, the term of this patent is extended or adjusted under 35 U.S.C. 154(b) by 370 days.

(21) Appl. No.: 13/051,076

(22) Filed: Mar. 18, 2011

(65) Prior Publication Data

US 2011/0165234 A1 Jul. 7, 2011

Related U.S. Application Data

(62) Division of application No. 12/313,340, filed on Nov. 19, 2008, now Pat. No. 7,931,915, which is a division of application No. 10/715,219, filed on Nov. 17, 2003, now Pat. No. 7,470,435.

(51) Int. Cl.
| | |
|---|---|
| *A61K 9/28* | (2006.01) |
| *A61K 9/48* | (2006.01) |
| *A61K 9/52* | (2006.01) |
| *A61K 9/54* | (2006.01) |
| *A61K 9/20* | (2006.01) |
| *A61K 31/135* | (2006.01) |
| *A01N 33/02* | (2006.01) |
| *C07C 211/00* | (2006.01) |
| *C09B 11/02* | (2006.01) |

(52) U.S. Cl.
USPC ........... 424/474; 424/451; 424/452; 424/457; 424/458; 424/462; 424/463; 424/464; 424/465; 424/468; 424/469; 424/472; 424/489; 424/490; 424/497; 514/648; 514/649; 564/316; 564/336

(58) Field of Classification Search
USPC ......... 424/474, 451, 452, 457, 458, 462, 463, 424/464, 465, 468, 469, 472, 489, 490, 424/497; 514/648, 649
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,535,186 A | 8/1985 | Husbands et al. | |
| 4,761,501 A | 8/1988 | Husbands et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,674,533 A | 10/1997 | Santus et al. | |
| 5,733,566 A | 3/1998 | Lewis | |
| 5,916,923 A | 6/1999 | Rudolph et al. | |
| 6,048,547 A | 4/2000 | Seth et al. | |
| 6,274,171 B1 | 8/2001 | Sherman et al. | |
| 6,294,192 B1 | 9/2001 | Patel et al. | |
| 6,342,533 B1 | 1/2002 | Jerussi et al. | |
| 6,352,721 B1 | 3/2002 | Faour | |
| 6,383,471 B1 | 5/2002 | Chen et al. | |
| 6,403,120 B1 | 6/2002 | Sherman et al. | |
| 6,419,958 B2 | 7/2002 | Sherman et al. | |
| 6,444,708 B2 | 9/2002 | Rudolph et al. | |
| 6,569,463 B2 | 5/2003 | Patel et al. | |
| 6,607,751 B1 | 8/2003 | Oidi et al. | |
| 6,645,528 B1 | 11/2003 | Straub et al. | |
| 8,268,352 B2 * | 9/2012 | Vaya et al. | 424/469 |
| 2002/0025339 A1 | 2/2002 | Sherman et al. | |
| 2003/0152627 A1 | 8/2003 | Beckert et al. | |
| 2006/0003004 A1 * | 1/2006 | Hirsh et al. | 424/468 |

FOREIGN PATENT DOCUMENTS

| | | |
|---|---|---|
| WO | WO 00/71099 | 11/2000 |
| WO | WO 03/041692 | 5/2003 |

OTHER PUBLICATIONS

Sheikh, Humera N., "Written Opinion of the International Searching Authority" in PCT/US04/36083, Jan. 11, 2005, 3 pgs, International Searching Authority, Alexandria, VA.

Baharlou, Simin, "International Preliminary Report on Patentability" for PCT/US04/036083, Aug. 7, 2006, 4 pgs., International Bureau of WIPO, Geneva, Switzerland.

Sproll, Susanne, "Supplemental European Search Report" in EP 04796796, Sep. 7, 2007, 2 pgs., European Patent Office, Munich Germany.

\* cited by examiner

*Primary Examiner* — Jane C Oswecki

(74) *Attorney, Agent, or Firm* — Florek & Endres PLLC

(57) ABSTRACT

A controlled release dosage form of venlafaxine that comprises an immediate release pellet and an extended release pellet.

14 Claims, No Drawings

EXTENDED RELEASE VENLAFAXINE FORMULATION

CROSS REFERENCE TO RELATED APPLICATIONS

The present application is a divisional application of U.S. patent application Ser. No. 12/313,340, which was originally filed on Nov. 19, 2008, which was a divisional of U.S. patent application Ser. No. 10/715,219, which was originally filed on Nov. 17, 2003, and which issued as U.S. Pat. No. 7,470,435.

BACKGROUND OF THE INVENTION

1. Field of the Invention

The present invention belongs to the field of pharmaceutical science, and provides an oral controlled release dosage formulation containing venlafaxine hydrochloride.

2. Description of the Related Art

Venlafaxine hydrochloride is described in U.S. Pat. Nos. 4,535,186; 4,761,501 and 6,342,533 which teach the production of venlafaxine and its analogues and are incorporated herein by reference. Venlafaxine hydrochloride is marketed as an antidepressant and for the treatment of Generalized Anxiety Disorder. Other uses include prevention of major depressive disorder relapse, bipolar and manic disorders, post traumatic stress disorder, late luteal phase dysphoric disorder, Gilles de la Tourette syndrome, bulimia nervosa or Shy Drager Syndrome, attention deficit disorder, Parkinson's disease, epilepsy, cerebral function disorders, obesity and weight gain, incontinence, dementia and related disorders. It is the preferred antidepressant where weight gain is problematic, as it is with the selective serotonin reuptake inhibitors (SSRIs). Venlafaxine hydrochloride is a phenylethylamine-derivative chemically unrelated to other currently available antidepressants (e.g., selective serotonin-reuptake inhibitors, tricyclics, tetracyclics). It is designated (R/S)-1-[2-(dimethylamino)-1-(4-methoxyphenyl)ethyl]cyclohexanol hydrochloride and has the empirical formula $C_{17}H_{27}NO_2 \cdot HCL$. Venlafaxine has a pKa of 9.4 and has a water solubility of 572 mg/mL.

The neurochemical mechanism of the antidepressant effect is believed to be potentiation of neurotransmitter activity in the central nervous system (CNS). Venlafaxine and its active metabolite, O-desmethylvenlafaxine (ODV), are potent inhibitors of neuronal serotonin and norepinephrine reuptake and weak inhibitors of dopamine reuptake. Venlafaxine does not inhibit monoamine oxidase and has no significant affinity for muscarinic, histaminergic or alpha-1 adrenergic receptors.

The drug is useful in the treatment of depressive affective disorders (e.g. major depression) at dosages of 37.5 to 375 mg daily (dosages exceeding 375 mg daily of extended release tablets are not recommended). The drug is available in both immediate-release tablets (EFFEXOR®) and extended-release capsules (EFFEXOR® XR). The sustained release capsules are available in 37.5, 75 and 150 mg capsules administered in a single dose either in the morning or in the evening at approximately the same time each day. If desired, patients with depression who are undergoing treatment with a therapeutic dose of conventional tablets may be switched to the extended-release capsules at the nearest equivalent daily venlafaxine dose (e.g., 37.5 mg twice daily to a 75 mg extended-release capsule once daily). To minimize gastrointestinal intolerance, it is recommended that the drug be taken with food. However, neither food nor time of administration has been found to effect bioavailability of venlafaxine or its active metabolite. On the basis of mass balance studies, at least 92% of a single oral dose of venlafaxine is absorbed. The absolute bioavailability is about 45% and plasma protein binding is approximately 30%. Venlafaxine and its active metabolite, ODV have an elimination half-life (T½) of 5±2 and 11±2 hours, respectively.

Administration of the immediate release tablets at a dosage of 75 mg every twelve hours results in a $C_{max}$ of 225 ng/ml and 290 ng/ml for venlafaxine and ODV, respectively. $T_{max}$ was 2 hours for venlafaxine and 3 hours for ODV. Administration of the extended release capsules provides a slower rate of absorption but the same extent of absorption compared with immediate release tablets. A 150 mg dose of the extended release capsules results in a lower $C_{max}$ (150 ng/ml for venlafaxine and 260 ng/ml for ODV) than for immediate release venlafaxine tablets. $T_{max}$ for the extended release capsules was 5.5 hours and 9 hours for venlafaxine and ODV, respectively. Steady-state concentrations of venlafaxine and ODV are attained within three days of oral multiple dose therapy. Plasma concentrations are altered by hepatic and renal impairment but unaltered by gender and age. Poor metabolizers, i.e. patients with low CYP2D6 levels have increased levels of venlafaxine and reduced levels of ODV than extensive ("normal") metabolizers. However, there is no need for dosage adjustment because of similar areas under the curve (AUCs). The commercially available product is a racemic mixture of the (+) and (−) enantiomers of veniafaxine. All the metabolites are racemic.

Numerous techniques exist in the prior art for preparing sustained or controlled release pharmaceutical formulations. Controlled release means or delivery devices that are well known to those of ordinary skill in the art, are described, for example in U.S. Pat. Nos. 3,845,770; 3,916,899; 3,536,809; 3,598,123; 4,008,719; 5,674,533; 5,059,595; 5,591,767; 5,120,548; 5,073,543; 5,354,556; 5,733,566 and 6,403,120 the disclosures of which are incorporated herein by reference.

U.S. Pat. No. 6,048,547 discloses a sustained-release venlafaxine hydrochloride pharmaceutical composition where venlafaxine and microcrystalline cellulose are combined with polyethylene oxide (PEO) and compressed into tablets.

Controlled release of the commercially available extended release venlafaxine hydrochloride capsules (EFFEXOR® XR) is achieved by diffusion through the coating membrane on the spheroids and is not pH dependent. EFFEXOR® XR is available in a once daily dosage form of venlafaxine which contains cellulose, ethylcellulose, gelatin, hydroxypropyl methylcellulose, iron oxide, and titanium dioxide.

The need also exists for a simply and economically produced pharmaceutical preparation which provides a pulsatile delivery system (immediate release followed by sustained release) which attains peak plasma levels, in the manner of an immediate release product, i.e earlier than a controlled release formulation, followed by sustained release over 24 hours. This results in allowing greater flexibility in designing sustained release profiles and providing improved plasma levels wherein the maximum plasma concentration ($C_{max}$) can be substantially reduced without a concomitant reduction in the area under the curve (AUC) and without prolongation of the time in which the maximum plasma concentration is obtained ($T_{max}$). Such a delivery dosage form has a practical application, and it represents a valuable contribution to the pharmaceutical arts. The present invention provides such a composition, and offers an efficient and cost effective method of preparation.

The present invention was created through efforts to solve the above problems, as well as other problems, and provides a superior pellet formulation of venlafaxine, its pharmaceutically acceptable salts and its active metabolite o-desmethyl venlafaxine (ODV).

Accordingly, it is an object of this invention to provide an oral pharmaceutical formulation of venlafaxine hydrochloride or its active metabolite (ODV) suitable for once daily administration that obtains its maximum plasma levels in less than 4 hours.

It is a further object of the present invention to provide a once a day pharmaceutical formulation that will provide 24 hour control of symptoms of depression or Generalized Anxiety Disorder.

The present invention relates to a new sustained release venlafaxine or its active metabolite pharmaceutical composition producing novel blood plasma levels which is not disclosed in, not rendered obvious by, previous patents nor elsewhere in the art. Other objects, features and advantages of the invention are not taught in the prior art, but will be more apparent to those versed in the art from the following specification, taken in conjunction with the drawings.

SUMMARY OF THE INVENTION

The active ingredients of this invention include venlafaxine, its active metabolite (ODV) and their analogs. For the purposes of this disclosure, and the claims that follow, the use of venlafaxine is understood to include the free base and pharmaceutically acceptable salt forms of venlafaxine, the racemate and its individual enantiomers, and venlafaxine analogs, both as racemates and as their individual enantiomers.

A preferred embodiment of the present invention involves the application of a venlafaxine and a binder onto inert spheres to form an immediate release pellet. Extended-release pellets are then formed by coating the immediate release pellets with a water-insoluble film forming polymer. The release rate of the drug from the extended release pellet is controlled by the thickness of the coating and the composition of the coating. The final formulation comprises a mixture of immediate release and extended release pellets. The venlafaxine hydrochloride release profile of the final formulation is controlled by varying the amounts of non-coated immediate release pellets and extended-release pellets. The immediate release and extended release pellets may be placed into a capsule or formed into a tablet using conventional tablet forming techniques.

Generally, the weight ratio of the immediate release pellets to the extended release pellets will be from about 90:10 to about 10:90, although a weight ratio of from about 20:80 to about 80:20 is preferred. The most preferred dosage form comprises about 25-50 weight percent of immediate release pellets and about 50-75 weight percent extended release pellets.

In a preferred embodiment, the dosage form will be administered once a day, ideally with or after a meal, and provide therapeutic levels of the drug throughout the day with peak plasma levels being obtained in less than five hours, preferably between 1-4 hours and most preferably between 2-3 hours, after administration. The usual dosage range is 75-375 mg.

DETAILED DESCRIPTION OF THE INVENTION

The invention provides a controlled release venlafaxine formulation for oral administration, said formulation comprising:

(1) an immediate release pellet comprising:
  (a) venlafaxine, its active metabolite, their isomers, or pharmaceutically acceptable salts thereof;
  (b) an inert pellet as a starting material; and
  (c) a binder; and
(2) extended release pellet comprising:
  (i) a core comprising:
    (a) venlafaxine, its active metabolite, their isomers, or pharmaceutically acceptable salts thereof;
    (b) an inert pellet as a starting material; and
    (c) a binder; and
  (ii) a coating comprising:
    (a) a water insoluble film-forming polymer; and
  (iii) optionally a second coating comprising:
    (a) a second film forming water insoluble polymer;

The formulation of the present invention is preferably based on active pellets having a core comprising any of the commonly known pellet starting material such as starch, sugar, microcrystalline cellulose, glass, vegetable gums or waxes having a diameter ranging from about 15 to about 60 mesh, preferably from about 20 to about 40 mesh. The preferred pellet starting material is sugar spheres, NF containing not less than about 62.5 percent and not more than about 91.5 percent of sucrose. The primary characteristic of the inert pellet is that it does not adversely react with venlafaxine, the other possible excipients in the pellet or the patient who will ultimately ingest the pellet. Further, the spheres should have consistent bulk density, low friability, and low dust generation properties.

An active drug layer is applied onto the inert pellets by spraying a suspension or solution comprising venlafaxine and a binder. The binder preferably is a film-forming polymer that possesses high adhesivity and an appropriate viscosity, to assure good adhesion between the sugar cores and venlafaxine particles. The binding agents employed can be any film-forming binding agent commonly known in the art such as cellulose ethers (e.g. ethyl cellulose), polyoxides, polyacrylates, polyethylene, polypropylene, polyurethane, hydroxypropyl methylcellulose, hydroxypropyl cellulose and polyvinylpyrrolidone. Mixtures of the aforementioned binding agents may also be used. In a preferred embodiment of the present invention, the film-forming binding agent is a water insoluble polymer such as ethylcellulose. In a second embodiment of the invention, a film-forming water soluble binder may be combined with the water insoluble binder. The preferred film-forming water soluble binding agent is polyvinylpyrrolidone (PVP) or hydroxypropyl methylcellulose.

The active pellets of the present invention will preferably comprise the following ingredients:

| INGREDIENT | PREFERRED | MOST PREFERRED |
| --- | --- | --- |
| venlafaxine | 30-80% | 45-70% |
| binder | 1-20% | 2-15% |
| starting pellets | 20-70% | 30-50% |

All the percentages in the above table are based on the total weight of the active pellets. If a combination of water insoluble and water soluble binders are used the water insoluble binder should be less than 50% of the total binder, preferably less than 40% and most preferred less than 35%.

The active drug layer is applied onto the inert pellet using any of the layering techniques known in the industry such as fluidized bed coating, rotor granulation or pan coating. A preferred method for applying active layer onto the inert pellet is the classic fluidized bed coating device, which consists simply of a vertical cylinder with an air-permeable bottom. The cylinder is charged with the inert pellets to be coated, sufficient volume of air is drawn through the bottom of the cylinder to suspend the mass of inert pellets, and the liquid to be applied is sprayed onto the inert pellets. The temperature of the fluidized air is balanced against the spray rate to maintain the inert pellets at the desired level of moisture and stickiness while the active coating is built up.

Once the active drug layer is applied onto the inert pellet, the product is referred to as the immediate release pellet or active pellet.

The immediate release pellets are coated with an extended release coating composition comprising a water insoluble polymer (preferably a polymethacrylate), and conventional processing aids such as a surfactant, an antisticking agent, and a plasticizer to form an extended release coating on the active pellets. The release of the drug from the extended release pellet is primarily controlled by the diffusion of the drug through the polymer coating. The extended release pellets preferably comprise from about 20 to about 90 weight percent of the total pellets in the final dosage formulation, preferably from about 40 to about 80 weight percent, and most preferably from about 60 to about 75 wt %.

The water insoluble polymer is preferably a polymethacrylate, methacrylic acid copolymers, methacrylate ester copolymers, acrylic acid or mixtures thereof. Eudragit® NE 30D, was found to be a suitable polymer for the present invention. Other preferred water insoluble polymers are cellulose esters, cellulose ethers, or cellulose ester-ethers such as ethyl cellulose, cellulose acylate, cellulose deacylate, cellulose triacylate, cellulose acetate, cellulose acetate butyrate, cellulose diacetate, cellulose triacetate, mono- di- and tri-cellulose arylates, and the like. Additional water insoluble polymers for forming the outer coating comprise cellulose acetaldehyde dimethyl acetate, cellulose acetate ethylcarbamate, cellulose acetate methylcarbonate, cellulose dimethylaminoacetate, semipermeable polyamide, polyvinyl acetate, semipermeable polyurethanes, semipermeable sulfonated polystyrenes, crosslinked selectively semipermeable polymers formed by the coprecipitation of an anion and a cation.

The water-insoluble polymer should comprises about 40 to about 99 percent of the extended-release coating, preferably about 50 to about 90 percent and most preferably about 60 to about 85 percent.

In an alternative embodiment of the present invention, two extended release coatings are applied to the immediate release pellets. The first extended release coating comprises a polymethacrylate, methacrylic acid copolymer, methacrylate ester copolymer, acrylic acid or mixtures thereof and the second extended release coating comprises a cellulose ester, a cellulose ether, or a cellulose ester-ether.

The extended release coatings applied to the immediate release pellets may optionally include a surfactant. The surfactant is selected from anionic, cationic, amphoteric and nonionic surfactants, including dialkyl sodium sulfosuccinate, polyoxyethylene glycerol, polyoxyethylene steryl ether, propoxy-ethoxy copolymer, polyoxyethylene fatty alcohol ester, polyoxyethylene sorbitan fatty acid esters, ethoxylated hydrogenated castor oil and butoxylated hydrogenated castor oil. The preferred surfactant is polysorbate 80 (Tween 80). If a surfactant is employed in the extended release coating it should be used in a concentration of 30 weight percent or less based upon the total weight of the extended release coating. The preferred amount of surfactant is preferably about 0.01 to about 20 percent and most preferably about 0.1 to about 10 percent of the extended-release coating.

The extended release coating may also optionally include an anti-sticking agent. The anti-sticking agent can be chosen from any of the known agents such as those selected from the group consisting of an alkaline earth metal stearate, glyceryl monostearate or talc. The preferred anti-sticking agents are talc and magnesium stearate. If used in the extended release coating, the anti-sticking agent should comprise about 1 to about 15 percent, and most preferably about 2 to about 10 percent, based on the total weight of the extended-release coating. A combination of anti-sticking agents such as talc and magnesium stearate may be used in the present invention.

The extended release coatings may also optionally include a plasticizer to reduce the brittleness of the coatings. Plasticizers which may be used include any of those known to those skilled in the art which are compatible with cellulose acetate, including but not limited to, acetyltributyl citrate, triacetin, acetyltriethyl citrate, dioctylphthalate, dibutylphthalate, triethyl citrate, tributylcitrate, polyethylene glycol, propylene glycol and mixtures thereof. The preferred plasticizer is triacetin. If a plasticizer is used in the extended release coating, the amount used should range from about 0.01 to about 30 percent based on the total weight of the extended-release coating, preferably about 0.1 to about 15 percent of the extended-release coating.

The extended release coatings are applied to the active pellets by forming a solution or suspension of the respective polymer and processing aids in a solvent such as acetone, isopropyl alcohol, or water and employing any of the application techniques known to those skilled in the art, such as fluidized bed coating, rotor granulation or pan coating. The preferred method is the fluidized bed. The choice of duration of mixing, the apparatus, the screens and other operating conditions is a matter for the normal skill and judgment of a person skilled in the art. Extended release pellets are dried in an oven at about 60° C. for about 40 hours.

A second coating may be added to the extended release pellets comprising a water insoluble polymer, an antisticking agent and a plasticizer. Examples of these excipients are listed above. Preferably the water insoluble polymer is cellulose acetate, the antisticking agent is talc and the plasticizer is triacetin. The coating is applied using the same apparatus and procedure used to prepare the extended release pellets above.

If the second extended release coating is employed it should comprises about 2-10 weight percent, preferably 3-7 weight percent of the extended release pellet and the first extended release coating should comprise about 10-50 weight percent, preferably, 15-40 weight percent of the total weight of the extended release pellets.

The final dosage form contains a mixture or blend of immediate release pellets and extended release pellets that are placed into a gelatin capsule. By varying the ratios of the two pellet, novel dissolution profiles and plasma profiles may be obtained. Alternatively, the immediate and extended release pellets can be further mixed with conventional tablet excipients and formed into tablets.

The drug is released from the final dosage form in a pulsatile manner with a portion released immediately and a portion released slowly and steadily for a prolonged period of up to 24 hours. The rate of venlafaxine release was determined according to the USP 26 standard procedures employing a Type 2 Apparatus, at 50 rpm with distilled water at 37° C. The controlled release dosage forms prepared according to the present invention should exhibit the following dissolution profile when tested according to the above described procedure:

| Time (hours) | Preferred | Most Preferred |
|---|---|---|
| 1 | 0-55% | 20-40% |
| 4 | 20-60% | 30-50% |
| 8 | 25-80% | 35-70% |
| 12 | NLT 30% | NLT 35% |
| 24 | NLT 50% | NLT 60% |

NLT = not less than

The following examples illustrate the present invention and are not intended to limit the scope of the present invention.

EXAMPLE 1

A controlled release oral venlafaxine HCl dosage form in accordance with the present invention is prepared by first forming immediate release pellets having the following composition:

I Immediate Release Pellets

| | % Total Weight |
|---|---|
| venlafaxine HCL | 60% |
| sugar sphere 30/35 | 35% |
| ethylcellulose (EC 10 Cps) | 5% |

Immediate release pellets of venlafaxine HCl are formed by dissolving ethylcellulose (EC 10 cps) in isopropyl alcohol and suspending venlafaxine HCl in the ethylcellulose solution to make a suspension of 25% solid content. The active drug suspension is then sprayed onto the sugar spheres 30/35 in a fluidized bed processor with a Wuster insert until the seeds are uniformly coated with the desired drug potency. The immediate release pellets are then dried in a fluidized bed processor until the moisture level, as measured by the loss on drying, is below 2%. The immediate release pellets are then passed through a 14 mesh screen and a 25 mesh screen and pellets are collected that are sized between 14 mesh and 25 mesh.

II. Extended Release Pellets

About two third of the immediate-release pellets from Step I above are used to prepare extended release pellets with the following composition:

| | |
|---|---|
| immediate release pellets (from Step I above) | 63.38% |
| talc | 4.58% |
| magnesium stearate | 4.58% |
| Tween 80 | 0.05% |
| Eudragit NE 30D | 27.41% |

First the talc is suspended in purified water. In a separate vessel, Tween 80 is added to isopropyl alcohol followed by magnesium stearate. The talc suspension is added to the magnesium stearate suspension. The talc-magnesium stearate suspension is then added to the Eudragit NE 30D suspension. The suspension is then sprayed onto the immediate release pellets in a fluidized bed processor with a Wuster insert to form the extended release pellets having approximately a 36% coating level. The extended release pellets are dried in the fluidized bed processor until the LOD (loss on drying) is less than 1%. The extended release pellets are mixed with 2% (w/w) talc for 10 minutes and subsequently cured at 60° C.±5° C. for about 40 hours. The cured pellets are passed through 14 and 25 mesh screens. The pellets retained on the 25 mesh screen are used in the formulation.

The immediate release pellets prepared in step I and extended release pellets prepared in step II are encapsulated. The final encapsulated dosage form contains 150 mg of venlafaxine base with the immediate release pellets comprising 55.5 mg of venlafaxine base and the extended release-pellets comprising 94.5 mg of venlafaxine base.

The resulting venlafaxine capsules were then tested according to the USP 26 dissolution test (type 2) at 50 rpm, at 37° C. in distilled water and found to have the following release profile:

TABLE 1

| Time (hours) | % Released |
|---|---|
| 0.25 | 37 |
| 0.5 | 37 |
| 1 | 37 |
| 2 | 37 |
| 4 | 37 |
| 6 | 37 |
| 8 | 38 |
| 12 | 42 |
| 20 | 60 |
| 24 | 68 |

The venlafaxine capsules produced in Example 1 were administered to human patients. Venlafaxine was first detected in the plasma at about 15 minutes after administration, and showed sustained release over 24 hours. The testing involved two groups of randomly selected patients that received either the venlafaxine formulation prepared in this Example or EFFEXOR® XR 150 mg in an open, randomized crossover single dose fasting study. Blood samples were collected over a 72 hour period and analyzed for venlafaxine concentrations. EFFEXOR® XR was the reference product and is a commercially available pharmaceutical product containing venlafaxine HCl. The results are given in Table 2.

TABLE 2

| | Test Mean | Ref. Mean | G-Mean Ratio |
|---|---|---|---|
| FASTING (N = 5) | | | |
| $C_{max}$ (ng/ml) | 50.810 | 67.799 | 0.718 |
| $AUC_{TLQC}$ (ng hr/ml) | 633.699 | 882.542 | 0.749 |
| $T_{max}$ (hr) | 1.827 | 6.359 | 0.287 |
| FED (N = 5) | | | |
| $C_{max}$ (ng/ml) | 83.92 | 96.44 | 0.866 |
| $AUC_{TLQC}$ (ng hr/ml) | 1476.69 | 1458.26 | 1.01 |
| $T_{max}$ (hr) | 3.292 | 6.403 | 0.514 |

EXAMPLE 2

A controlled release venlafaxine formulation in accordance with the present invention is prepared by first forming immediate release pellets having the following composition:

I. Immediate Release Pellets

| | % Total Weight |
|---|---|
| venlafaxine hydrochloride | 60.0 |
| sugar spheres | 34.0 |
| PVP (K-30) | 4.0 |
| EC 10 cps | 2.0 |

Immediate release pellets of venlafaxine HCl are formed by dissolving ethylcellulose (EC 10 cps) and the PVP (K-30) in isopropyl alcohol and suspending venlafaxine HCl in the ethylcellulose/PVP solution to make a suspension of 30% solid content. The active drug suspension is then sprayed onto the sugar spheres 30/35 in a fluidized bed processor with a Wuster insert until the seeds are uniformly coated with the desired drug potency. The immediate release pellets are then dried in a fluidized bed processor until the moisture level, as measured by the loss on drying, is below 2%. The immediate release pellets are then passed through a 14 mesh screen and a 25 mesh screen and pellets are collected that are sized between 14 mesh and 25 mesh.

II. Extended Release Pellets

Extended release pellets in accordance with the present invention are prepared using a portion of the immediate release pellets prepared in Step I above. The extended release pellets have the following composition:

|  | % TOTAL WT. |
| --- | --- |
| immediate release pellets (Step I) | 79.37 |
| talc | 2.58 |
| magnesium stearate | 2.58 |
| tween 80 | 0.03 |
| Eudragit NE 30D | 15.44 |

The extended release pellets are prepared according to the procedure described in Example 1 except the immediate release beads are coated until a 22% theoretical coating level is obtained.

The strength of the final encapsulated product is 150 mg of venlafaxine base with the immediate release pellets comprising 55.5 mg of venlafaxine base and the extended release pellets comprising 94.5 mg of venlafaxine base.

The resulting venlafaxine capsules were then tested according to the USP 26 dissolution test (type 2), at 50 rpm, at 37° C., in distilled water and found to have the following release profile:

TABLE 3

| Time (hours) | % Released |
| --- | --- |
| 0.25 | 35 |
| 0.50 | 36 |
| 1 | 36 |
| 2 | 36 |
| 4 | 37 |
| 8 | 63 |
| 12 | 86 |
| 20 | 99 |
| 24 | 101 |

The venlafaxine capsules produced in this Example were administered to human patients. Venlafaxine showed a sustained release over 24 hours. The results of the in vivo provided are given in Tables 4 and 5.

TABLE 4

| FASTING (N = 5) | | | |
| --- | --- | --- | --- |
|  | Test Mean | Ref. Mean | G-Mean Ratio |
| $C_{max}$ (ng/ml) | 108.30 | 89.32 | 1.21 |
| $AUC_{TLQC}$ (ng hr/ml) | 1486.68 | 1211.56 | 1.23 |
| $T_{max}$ (hr) | 4.458 | 6.00 | 0.743 |

TABLE 5

| FED (N = 6) | | | |
| --- | --- | --- | --- |
|  | Test Mean | Ref. Mean | G-Mean Ratio |
| $C_{max}$ (ng/ml) | 119.06 | 94.74 | 1.26 |
| $AUC_{TLQC}$ (ng hr/ml) | 1624.90 | 1358.30 | 1.20 |
| $T_{max}$ (hr) | 5.00 | 4.83 | 1.03 |

EXAMPLE 3

A controlled release venlafaxine formulation in accordance with the present invention is prepared by first forming immediate release pellets having the following composition:

I. Immediate Release Pellets

|  | % Total Weight |
| --- | --- |
| venlafaxine hydrochloride | 60.0 |
| sugar spheres | 35.0 |
| EC 10 cps | 5.0 |

The immediate release pellets are prepared according to the procedure described in Example 1.

II. Extended Release Pellets

Extended release pellets in accordance with the present invention are prepared using a portion of the immediate release pellets prepared in Step I above. The extended release pellets have the following composition:

|  | % TOTAL WT. |
| --- | --- |
| immediate release pellets (Step I) | 71.00 |
| talc | 3.62 |
| magnesium stearate | 3.62 |
| tween 80 | 0.04 |
| Eudragit NE 30D | 21.71 |

The extended release pellets are prepared according to the procedure described in Example 1.

A second extended release coating is applied to the extended release pellets prepared in step II. The second coated extended release pellets then have the following composition:

III. Second Coating

|  | % TOTAL WT. |
| --- | --- |
| venlafaxine extended pellets (Step II) | 96.0 |
| cellulose acetate | 2.42 |
| talc | 1.21 |
| triacetin | 0.36 |

The second coating is applied to the extended release pellets prepared in Step II using the same apparatus and procedure used to prepare the extended release pellet. The pellets sized between #14 and #25 mesh are collected.

108 mg of the immediate release pellets and 258.2 mg of the extended release pellets are then encapsulated to give a final dosage form that contains approximately 150 mg of venlafaxine base.

The resulting venlafaxine capsules were then tested according to the USP 26 dissolution test (type 2), at 50 rpm, at 37° C., in distilled water and found to have the following release profile:

TABLE 6

| Time (hours) | % Released |
|---|---|
| 0.25 | 36 |
| 0.50 | 37 |
| 1 | 37 |
| 2 | 38 |
| 4 | 39 |
| 6 | 44 |
| 8 | 51 |
| 12 | 65 |
| 20 | 83 |
| 24 | 89 |

The venlafaxine capsules produced in this Example were administered to human patients according to the procedure described in Example 1. The results provided given in Table 7.

TABLE 7

| FASTING (N = 8) | | | |
|---|---|---|---|
| | Test Mean(CV) | Ref. Mean(CV) | G-Mean Ratio |
| $C_{max}$ (ng/ml) | 61.962 | 67.799 | 0.914 |
| $AUC_{0-48}$ (ng hr/ml) | 788.170 | 882.542 | 0.893 |
| $T_{max}$ (hr) | 1.938 | 6.359 | 0.305 |

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

The invention claimed is:

1. A controlled release composition consisting essentially of:
   (1) an immediate release pellet consisting essentially of:
      (a) 30-80% of venlafaxine, its o-desmethylvenlafaxine active metabolite, or pharmaceutically acceptable salts thereof;
      (b) 20-70% of an inert sugar pellet; and
      (c) 1-20% of a binder; and
   (2) an extended release pellet consisting essentially of:
      (i) a core consisting essentially of:
         (a) 30-80% of venlafaxine, its o-desmethylvenlafaxine active metabolite, or pharmaceutically acceptable salts thereof;
         (b) 20-70% of an inert sugar pellet; and
         (c) 1-20% of a binder;
      (ii) a coating surrounding the core consisting essentially of:
         (a) 40-99% of a water insoluble polymer;
         (b) 0-30% of a surfactant;
         (c) 0-15% of an antisticking agent; and
         (d) 0-30% of a plasticizer;
   wherein a single peak plasma concentration of the venlafaxine or o-desmethylvenlafaxine active metabolite is obtained in less than four hours after administration of the controlled release composition when administered in a single dose under fasting conditions, and the extended release pellets comprises about 40-80% of the controlled release composition.

2. The controlled release composition according to claim 1 wherein
   (1) the immediate release pellet consist essentially of:
      (a) 45-70% of venlafaxine, its o-desmethylvenlafaxine active metabolite, or pharmaceutically acceptable salts thereof;
      (b) 30-50% of an inert sugar pellet; and
      (c) 2-15% of a binder; and
   (2) the extended release pellet consist essentially of:
      (i) a core consisting essentially of:
         (a) 45-70% of venlafaxine, its o-desmethylvenlafaxine active metabolite, or pharmaceutically acceptable salts thereof;
         (b) 30-50% of an inert sugar pellet; and
         (c) 2-15% of a binder; and
      (ii) a coating consisting essentially of:
         (a) 50-90% of a water insoluble polymer;
         (b) 0.1-10% of a surfactant;
         (c) 2-10% of an antisticking agent; and
         (d) 0.1-15% of a plasticizer;
   wherein a single peak plasma concentration of the venlafaxine or o-desmethylvenlafaxine active metabolite is obtained in less than four hours after administration of the controlled release composition when administered in a single dose under fasting conditions and the extended release pellets comprises about 60-75% of the controlled release composition.

3. The controlled release composition according to claim 2 wherein the single maximum plasma concentration of venlafaxine or o-desmethylvenlafaxine active metabolite is obtained in about one to about four hours after administration of the controlled release composition when administered in a single dose under fasting conditions.

4. A controlled release composition for oral administration-comprising:
   (1) an immediate release pellet comprising:
      (a) venlafaxine, its o-desmethylvenlafaxine active metabolite, or pharmaceutically acceptable salts thereof;
      (b) an inert sugar pellet; and
      (c) a binder;
   (2) an extended release pellet comprising:
      (i) a core comprising:
         (a) venlafaxine, its o-desmethylvenlafaxine active metabolite, or pharmaceutically acceptable salts thereof;
         (b) an inert sugar pellet; and
         (c) a binder;
      (ii) a first coating surrounding the core comprising:
         (a) a water-insoluble polymer;
      (iii) a second coating surrounding the first coating comprising
         (a) a water-insoluble polymer;
         (b) a antisticking agent; and
         (c) a plasticizer.

5. The controlled release composition according to claim 4, wherein
   (1) the immediate release pellet comprises:
      (a) 30-80% of venlafaxine, its o-desmethylvenlafaxine active metabolite, or pharmaceutically acceptable salts thereof;
      (b) 20-70% of an inert sugar pellet; and
      (c) 1-20% of a binder; and (2) the extended release pellet comprises:
  (i) the core comprising:
    (a) 30-80% of venlafaxine, its o-desmethylvenlafaxine active metabolite, or pharmaceutically acceptable salts thereof;
    (b) 20-70% of an inert sugar pellet; and
    (c) 1-20% of a binder;
  (ii) the first coating comprises;
    (a) 40-99% of a water insoluble polymer;
    (b) 0-20% of a surfactant;
    (c) 0-15% of an antisticking agent; and
    (d) 0-30% of a plasticizer;
  (iii) the second coating comprises;
    (a) 30-90% of a water-insoluble polymer;
    (b) 5-50% of a antisticking agent; and
    (c) 1-20% of a plasticizer.

6. The controlled release composition according to claim 5 wherein
(1) the immediate release pellet comprises:
  (a) 45-70% of venlafaxine, its o-desmethylvenlafaxine active metabolite, or pharmaceutically acceptable salts thereof;
  (b) 30-50% of an inert sugar pellet; and
  (c) 2-15% of a binder; and
(2) the extended release pellet comprises:
  (i) the core comprising:
    (a) 50-70% of venlafaxine, its o-desmethylvenlafaxine active metabolite, or pharmaceutically acceptable salts thereof;
    (b) 30-50% of an inert sugar pellet; and
    (c) 2-15% of a binder; and
  (ii) the first coating comprises:
    (a) 50-90% of a water insoluble polymer;
    (b) 0.1-10% of a surfactant;
    (c) 2-10% of an antisticking agent; and
    (d) 0.1-15% of a plasticizer;
  (iii) the second coating comprises;
    (a) 45-70% of a water-insoluble polymer;
    (b) 20-40% of a antisticking agent; and
    (c) 5-15% of a plasticizer.

7. The controlled release composition according to claim 1 wherein the single maximum plasma concentration of venlafaxine or o-desmethylvenlafaxine active metabolite is obtained in about two to about three hours after administration of the controlled release composition when administered in a single dose under fasting conditions.

8. The controlled release composition according to claim 1 that exhibits the following dissolution profile when tested according to USP 26 with a Type 2 Apparatus at 50 rpm in distilled water at 37° C.:
  0-55% of the venlafaxine or o-desmethylvenlafaxine is released after one hour;
  20-60% of the venlafaxine or o-desmethylvenlafaxine is released after four hours;
  25-80% of the venlafaxine or o-desmethylvenlafaxine is released after eight hours; and
  not less than 50% of the venlafaxine or o-desmethylvenlafaxine is released after twenty four hours.

9. The controlled release composition according to claim 8 having the following dissolution profile when tested according to USP 26 with a Type 2 Apparatus at 50 rpm in distilled water at 37° C.:
  10-40% of the venlafaxine or o-desmethylvenlafaxine is released after one hour;
  30-50% of the venlafaxine or o-desmethylvenlafaxine is released after four hours;
  35-70% of the venlafaxine or o-desmethylvenlafaxine is released after eight hours; and
  not less than 60% of the venlafaxine or desmethylvenlafaxine is released after twenty-four hours.

10. The controlled release composition according to claim 4 wherein the maximum plasma concentration of venlafaxine or o-desmethylvenlafaxine is obtained in about two to about three hours.

11. The controlled release composition according to claim 4 that exhibits the following dissolution profile when tested according to USP 26 with a Type 2 Apparatus at 50 rpm in distilled water at 37° C.:
  0-55% of the venlafaxine or o-desmethylvenlafaxine is released after one hour;
  20-60% of the venlafaxine or o-desmethylvenlafaxine is released after four hours;
  25-80% of the venlafaxine or o-desmethylvenlafaxine is released after eight hours; and
  not less than 50% of the venlafaxine or o-desmethylvenlafaxine is released after twenty four hours.

12. The controlled release composition according to claim 11 having the following dissolution profile when tested according to USP 26 with a Type 2 Apparatus at 50 rpm in distilled water at 37° C.:
  10-40% of the venlafaxine or o-desmethylvenlafaxine is released after one hour;
  30-50% of the venlafaxine or o-desmethylvenlafaxine is released after four hours;
  35-70% of the venlafaxine or o-desmethylvenlafaxine is released after eight hours; and
  not less than 60% of the venlafaxine or desmethylvenlafaxine is released after twenty-four hours.

13. The controlled release composition according to claim 4 wherein the composition is a capsule.

14. The controlled release composition according to claim 4 wherein the composition is a tablet.

* * * * *